United States Patent [19]

Rinehart

[11] 4,443,628
[45] Apr. 17, 1984

[54] ANTIDOTAL COMPOUNDS FOR USE WITH HERBICIDES

[75] Inventor: Jay K. Rinehart, Akron, Ohio

[73] Assignee: PPG Industries, Inc., Pittsburgh, Pa.

[21] Appl. No.: 218,874

[22] Filed: Dec. 22, 1980

Related U.S. Application Data

[63] Continuation-in-part of Ser. No. 106,433, Dec. 26, 1979, abandoned.

[51] Int. Cl.$^3$ .......................................... C07C 103/127
[52] U.S. Cl. ...................................... 564/209; 71/100; 71/111; 71/118
[58] Field of Search ........................... 71/118; 564/209

[56] References Cited

U.S. PATENT DOCUMENTS

| | | | |
|---|---|---|---|
| 3,287,106 | 11/1966 | Chupp | 71/2.7 |
| 3,867,444 | 2/1975 | Baker | 260/561 HL |
| 3,931,313 | 1/1976 | Baker | 260/561 H |
| 3,966,811 | 6/1976 | Krenzer | 71/118 |
| 4,033,756 | 7/1977 | Hoffmann | 564/209 |
| 4,053,297 | 10/1977 | Richter | 71/88 |
| 4,110,101 | 8/1978 | Stach et al. | 71/88 |
| 4,113,464 | 9/1978 | Stach et al. | 71/88 |
| 4,116,670 | 9/1978 | Stach et al. | 71/88 |
| 4,137,070 | 1/1979 | Pallos et al. | 71/88 |
| 4,155,745 | 5/1979 | Walker | 71/90 |
| 4,195,036 | 3/1980 | Gozzo et al. | 564/209 |
| 4,261,733 | 4/1981 | Chupp | 71/118 |
| 4,294,764 | 10/1981 | Rinehart | 71/88 |
| 4,392,884 | 7/1983 | Pallos et al. | 71/100 |
| 4,400,197 | 8/1983 | Rinehart | 71/88 |

OTHER PUBLICATIONS

Hamm et al. I, "Effect of Variations, etc.", (1957), J. Ag. Food Chem. 5, pp. 30–32, (1957).
Hamm et al. II, "Relation of Herbicidal Activity, etc.", (1956), J. Ag. Food Chem. 4, pp. 518–522, (1956).

*Primary Examiner*—Glennon H. Hollrah
*Attorney, Agent, or Firm*—Edward J. Whitfield

[57] ABSTRACT

This invention relates to N-(2,2-dialkoxyethyl)-N-substituted-2-2-dichloroacetamides, their use as antidotes and herbicidal compositions containing these compounds.

2 Claims, No Drawings

ANTIDOTAL COMPOUNDS FOR USE WITH HERBICIDES

CROSS-REFERENCE TO RELATED APPLICATION

This application is a continuation-in-part of copending application Ser. No. 106,433 filed Dec. 26, 1979 now abandoned.

FIELD OF THE INVENTION

This invention relates to N-(2,2-dialkoxyethyl)-N-substituted-2,2-dichloroacetamides, their use as antidotes, and herbicidal compositions containing these compounds.

DESCRIPTION OF THE INVENTION

This invention relates to N-(2,2-dialkoxyethyl)-N-substituted-2,2-dichloroacetamides represented by the formula:

$$\begin{array}{c} Cl \\ \diagdown \\ \diagup \\ Cl \end{array} CH-\underset{\underset{O}{\|}}{C}-\underset{\underset{R}{|}}{N}-CH_2-CH \begin{array}{c} \diagup O-R^1 \\ \diagdown O-R^2 \end{array}$$

wherein:

R is methyl, ethyl, propyl, 1-methylethyl, 2-propenyl, 2-butenyl, 2-methyl-2-propenyl, 2-propynyl or 1,1-dimethyl-2-propynyl; and $R_1$ and $R_2$ are alkyl of up to 4 carbon atoms.

The compounds of this invention have been found eminently well-suited for protecting growing crops, for example, corn, from the phytotoxic effects of active herbicides, particularly S-alkyl thiocarbamate herbicides and chloroacetanilide herbicides. A compound of this invention that has been found to exhibit especially efficacious long-term, antidotal effects, i.e., lasting up to three weeks or more after application, is N-(2,2-dimethoxyethyl)-N-(2-propenyl)-2,2-dichloroacetamide, i.e., a compound wherein R is 2-propenyl and $R_1$ and $R_2$ are methyl.

It is, of course, to be understood that stereo and optical isomers of compounds represented by the above formula are contemplated within the scope of this invention.

The compounds of this invention may be prepared by reacting an N-(2,2-dialkoxyethyl) N-substituted amine of the formula:

$$HN-CH_2CH \begin{array}{c} \diagup O-R^1 \\ \diagdown \\ | \\ R \end{array} \begin{array}{c} \\ \diagdown O-R^2 \end{array}$$

wherein R, $R_1$ and $R_2$ are as defined hereinabove with an at least equimolar amount of dichloroacetyl chloride in the presence of an acid acceptor such as a tertiary amine, for example, triethylamine. Preferably the reaction is conducted in the presence of an inert organic solvent, for example, methylene chloride or benzene. The reaction is typically conducted at a temperature ranging from 0° C. to ambient, i.e., 20° C. to 23° C., for a time sufficient to obtain the desired extent of conversion, which may range from a few minutes to a few hours. At the completion of the reaction, the reaction mixture is washed with dilute acid, dried, and stripped of solvent. The product is typically obtained in liquid, substantially pure form, and generally does not require further purification.

The following Examples 1 through 3 are illustrative of the preparation of certain specific antidotal compounds of this invention.

EXAMPLE 1

Preparation of N-(2,2-dimethoxyethyl)-N-(2-propenyl)-2,2-dichloroacetamide

A three-neck flask was placed in an ice bath and charged with 2.9 grams (0.02 mole) of N-(2-propenyl)-N-(2,2-dimethoxyethyl)amine, and 2.02 grams (0.02 mole) of triethylamine in 100 milliliters of methylene chloride. To this stirred mixture, a solution of 2.95 grams (0.02 mole) of dichloroacetyl chloride in 5 milliliters of methylene chloride was added dropwise over a period of 15 minutes. The reaction mixture was stirred for one-half hour, removed from the ice bath, and stirred for an additional three hours, by which time the reaction mixture had reached ambient temperature. The reaction mixture was then washed with a 50 milliliter portion of 10 percent aqueous hydrochloric acid solution, dried over magnesium sulfate, and concentrated on a rotary evaporator at a temperature not in excess of 50° C., yielding 4.96 grams of a pale pink liquid identified by NMR spectroscopy as N-(2,2-dimethoxyethyl)-N-(2-propenyl)-2,2-dichloroacetamide.

EXAMPLE 2

Preparation of N-(2,2-dimethoxyethyl)-N-(1-methylethyl)-2,2-dichloroacetamide

When the procedure described in Example 1 was followed reacting 2.21 grams (0.015 mole) of N-(1-methylethyl)-N-(dimethoxyethyl)amine, 1.52 grams (0.015 mole) of triethylamine and 2.21 grams (0.015 mole) of dichloroacetyl chloride, 3.74 grams of a pale yellow oil was obtained, which was identified by NMR spectroscopy as N-(2,2-dimethoxyethyl)-N-(1-methylethyl)-2,2-dichloroacetamide.

EXAMPLE 3

Preparation of N-(2,2-dimethoxyethyl)-N-methyl-2,2-dichloroacetamide

When the procedure described in Example 1 was followed reacting 2.38 grams (0.02 mole) of N-(2,2-dimethoxyethyl)methanamine, 2.02 grams (0.02 mole) of triethylamine, and 2.95 grams (0.02 mole) of dichloroacetyl chloride, 4.68 grams of a pale yellow liquid was obtained which was identified by NMR spectroscopy as N-(2,2-dimethoxyethyl)-N-methyl-2,2-dichloroacetamide.

The mode of synethesis of specific compounds of this invention has been illustrated in some detail by the foregoing Examples: but it is to be understood that any compound contemplated to be within the scope of this invention may be prepared by those skilled in the art simply by varying the choice of starting materials using the illustrated techniques or other suitable techniques.

The compounds prepared as described in the foregoing examples as well as other compounds within the scope of this invention (which themselves are not significantly herbicidally active), are useful in reducing phytotoxic damage caused by active herbicides to growing crops, especially corn. The active herbicides which tend to phytotoxically damage corn, when used in herbicidally effective amounts against weeds growing among the corn crop, are S-alkyl thiocarbamate-type herbicides or chloroacetanilide-type herbicides, particularly the former. Exemplary of some S-alkyl thiocarbamate-type herbicides are S-ethyl diethylthiocarbamate, S-ethyl diisobutylthiocarbamate, S-ethyl dipropylthiocarbamate, and S-propyl dipropylthiocarbamate; whereas 2-chloro-2',6'-diethyl-N-(methoxymethyl)acetanilide, 2-chloro-N-isopropylacetanilide, 2-chloro-N,N-diallylacetamide, N-chloroacetyl-N-(2,6-diethylphenyl)glycine ethyl ester, 2-chloro-N-(2-ethyl-6-methylphenyl)-N-(2-methoxy-1-methylethyl)acetamide, and 2-chloro-2',3'-dimethyl-N-(methoxymethyl)acetanilide are examples of some chloroacetanilide-tupe herbicides.

The S-alkyl thiocarbamate herbicides or chloroacetanile herbicides are typically incorporated into the soil or growth medium prior to crop seeding, which technique is commonly referred to as "pre-plant incorporation." The antidotal compounds of this invention may be separately incorporated into the soil but are preferably formulated or composited with the S-alkyl thiocarbamate herbicide or the chloroacetanilide herbicide. In either case, sufficient of the antidotal compounds of this invention are present such that the weight ratio of herbicide to compound of this invention is in the range of 18:1 to 6:1, the herbicide, of course, being present in herbicidal amount, which depending on the weed species, may vary over a wide range. Typically the herbicide is used in amounts ranging from 0.56 or less kilogram per hectare (0.5 pound per acre) to 11.2 or more kilograms per hectare (10 pounds per acre).

It is to be further understood that mixtures of S-alkyl thiocarbamate herbicides and chloroacetanilide herbicides as well as mixtures of compounds of this invention may be used. In addition, the herbicide-antidotal compound formulations of this invention may contain other agronomically acceptable adjuvants such as inert carriers, herbicides other than S-alkyl thiocarbamates or chloroacetanilides, or other commonly used agricultural compounds, for example, pesticides, stabilizers, fertilizers, soil life extending agents, and the like.

The compounds of this invention, whether used as such or in formulation with other materials, may be applied to the soil in the form of dusts, granules, wettable powders, solutions, suspensions, aerosols, emulsions, dispersions, or the like in a manner well-known to the art.

The following Example 4 is illustrative of the antidotal effect exhibited by the compounds of this invention in protecting Funk's G-4288 hybrid field corn from the phytotoxic damage caused by a commercial herbicide, namely, S-ethyl dipropylthiocarbamate (commonly referred to as EPTC).

EXAMPLE 4

(a) Pulverized, sandy loam topsoil and coarse, washed cement sand screened to pass a 0.475 centimeter (3/16 inch) mesh screen were mixed in a weight ratio of three parts of soil to one part of sand, and the mix was pasteurized with live steam to kill any plants, pathogenic organisms, and natural weed seed populations.

Shallow containers, commonly referred to as "flats", were filled to within 0.95 centimeter (⅜ inch) of the top with the pasteurized soil mixture, leveled but not firmed, and were passed under a sprayer equipped with a fixed fan nozzle suspended over a speed adjustable movable belt. The fan nozzle operated at about 2,800 grams per square centimeter (40 psi) air pressure, delivering 25 milliliters of distilled water in 4.6 seconds. At 25.4 centimeters (10 inches) above the soil surface, a 45.7 centimeter (18 inches) wide spray pattern was applied. The belt speed was adjusted so as to travel 76.2 centimeters (30 inches) per revolution in 8.3 seconds. The soil test containers passed under the nozzle within 4.6 seconds. The area covered in this time was 0.63 square meter (6.75 square feet). The volume of liquid delivered was equivalent to 400 liters per hectare (42.6 gallons per acre) and 0.7029 grams of a 100 percent active test compound per 0.63 square meter (6.75 square feet) was equivalent to an application rate of 11.2 kilograms per hectare (10 pounds per acre) of active test compound.

The carrier solvent used for the S-alkyl thiocarbamate, i.e., EPTC, and the antidotal compound was a 90:8:2 volume/volume mixture of acetone:methanol:dimethylformamide. After the test container was sprayed with the test compound or mixture of compounds, it was immediately emptied into a clean plastic bag, the top secured, and the contents thoroughly mixed by hand agitation of the plastic bag, and the contents were then emptied back into the test container. The soil was then leveled, firmed, and seeded with Funk's G-4288 Hybrid Field Corn, and the soil mixture covered with a 2.54 centimeter (1 inch) layer of pasteurized screened sand. The treated flats were then transferred to the plant growth room, where they were lightly watered overhead as required to insure growth. The plant growth room was illuminated with a light intensity that averaged 27,000 lumens per square meter (2,500 foot-candles) at the growth level. The growth room was maintained at 29° C. to 30° C. during the 16-hour photo period, and 20° C. to 23° C. at night. The relative humidity of the growth room when less than one-third full averaged from 50 to 55 percent.

The treated flats were allowed to grow and injury, if any, to the corn was determined by visual inspection periodically thereafter. Injury was noted as reduction in growth, and/or as hormonal distortion as compared with an untreated control.

This hormonal injury is manifested as a distortion of the growing apex of the stem due to the failure of the developing leaves to unfurl from the growing shoot. Continued apical growth results in a compaction and distortion of the subapical tissues until a break is caused in the surrounding leaf tissue. Hormonal injury may occur in the initial seedling stages of growth when high concentration of S-alkyl thiocarbamate has been applied or at later growth stages with lower concentration of the herbicide. The distortion may not appear until the growing apex of the stem is above the soil line or may not appear until divides and begins formation of the pistillate inflorescens. Hormonal injury may also weaken the prop root system so as to cause the whole plant to collapse of its own weight.

(b) When EPTC was applied by pre-plant incorporation, as described in section (a) of this Example, at a rate of 6.72 kilograms per hectare (6 pounds per acre) with no antidotal compound added, the corn showed a 90 percent injury as indicated by a reduction in growth and hormonal distortion after 14 days, 25 days, 28 days, and 42 days. In addition, after 42 days, necrosis also developed to contribute to the injury of the corn crop.

(c) When EPTC at a rate of 6.72 kilograms per hectare (6 pounds per acre) and N-(2,2-dimethoxyethyl)-N-(2-propenyl)-2,2-dichloroacetamide (prepared as described in Example 1) at a rate of 0.56 kilograms per hectare (0.5 pound per acre) that is, a ratio of 12 parts by weight of EPTC to one part by weight of antidotal compound, were applied by pre-plant incorporation, as described in section (a) of this Example, the corn crop, after 42 days, was completely healthy and normal and showed no signs of growth reduction or hormonal distortion.

Although the invention has been described in considerable detail with reference to specific illustrative embodiments thereof, it is not intended that the invention be so limited except as set forth in the appended claims.

I claim:
1. A compound of the formula:

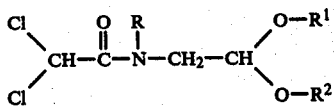

wherein:
R is 2-propenyl, 2-butenyl or 2-methyl-2-propenyl, and
$R^1$ and $R^2$ are alkyl of up to 4 carbon atoms.
2. The compound N-(2,2-dimethoxyethyl)-N-(2-propenyl)-2,2-dichloroacetamide.

* * * * *